(12) United States Patent
Oyaski

(10) Patent No.: US 6,410,818 B1
(45) Date of Patent: Jun. 25, 2002

(54) DEVICE AND METHOD FOR PROMOTING HEALING OF TOPICAL STRESS CRACKS

(76) Inventor: Michael F. Oyaski, 207 E. Highland Ave., Ebensburg, PA (US) 15931

( * ) Notice: Subject to any disclaimer, the term of this patent is extended or adjusted under 35 U.S.C. 154(b) by 0 days.

(21) Appl. No.: 09/736,595

(22) Filed: Dec. 12, 2000

(51) Int. Cl.[7] .......................... A61F 13/00; A61F 13/02; A61M 35/00
(52) U.S. Cl. ............................ 602/54; 602/42; 602/48; 604/289; 424/443; 424/448
(58) Field of Search .................. 424/400, 443, 424/445, 444, 446, 447, 448; 602/41–43, 48, 52, 54, 57; 604/239, 290, 304, 305, 306, 307, 308; 606/213, 214, 215

(56) References Cited

U.S. PATENT DOCUMENTS 5,259,835 A * 11/1993 Clark et al. .................... 602/48

* cited by examiner

Primary Examiner—Kim M. Lewis
(74) Attorney, Agent, or Firm—James Ray & Associates

(57) ABSTRACT

A device for promoting the healing of a topical stress crack in a predetermined skin portion of the body. The device comprising a first means engageable with a skin portion of the body for drawing such stress crack together. A screen member disposed intermediate with the skin crack and first means for maintaining closure of such skin crack. A medical adhesive engageable with a screen member as a means for sealing the stress crack together.

14 Claims, 1 Drawing Sheet

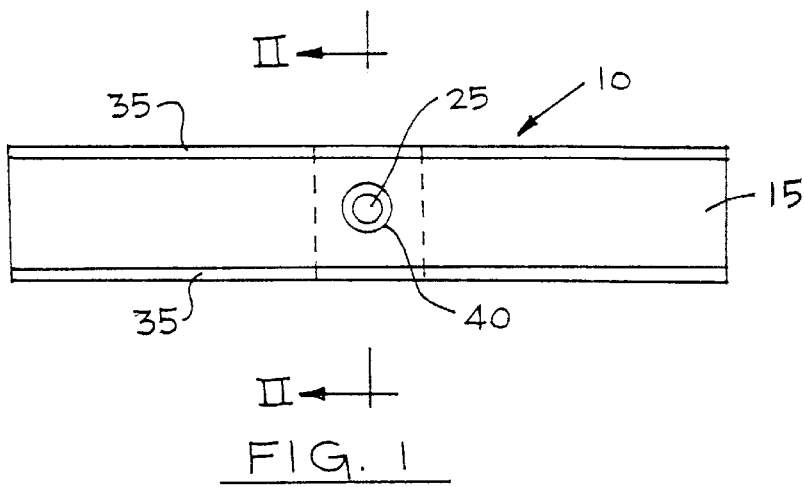
FIG. 1
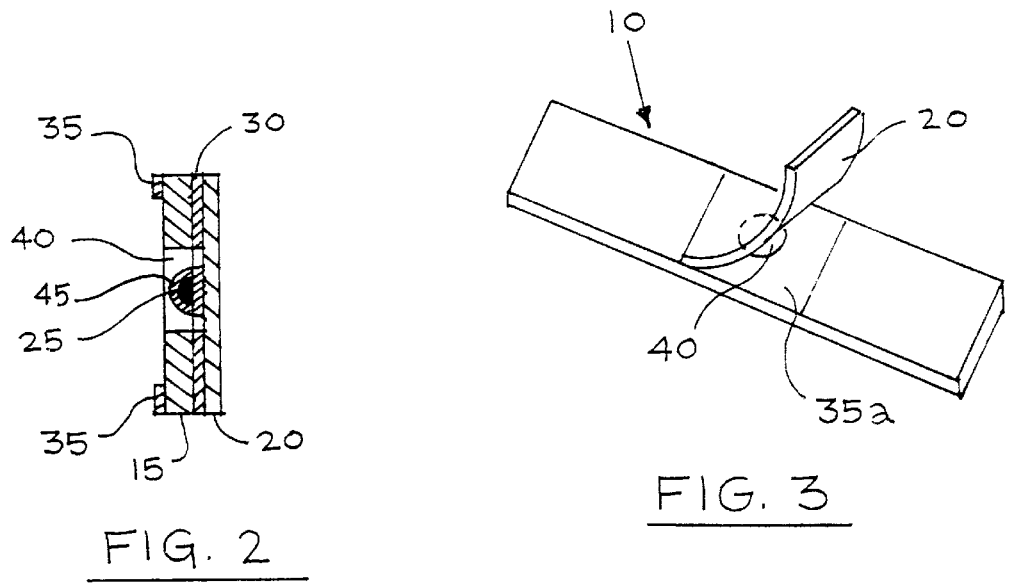
FIG. 2
FIG. 3

DEVICE AND METHOD FOR PROMOTING HEALING OF TOPICAL STRESS CRACKS

FIELD OF THE INVENTION

The present invention relates, in general, to stress cracks, and more particularly, to a device and method for enhancing the healing of topical stress cracks.

BACKGROUND OF THE INVENTION

Prior to the present invention, a stress crack that develops on the hands or feet is normally treated by applying an ointment or cream to soften the skin and induce healing. Because a stress crack is similar to an open wound on the skin, the crack is often painful and sometimes bleeds. It is also slow to heal because it is typically exposed to water, air, detergents, and other external elements. A bandage is sometimes used, but this acts merely as a cover which affords minimal protection from the above mentioned elements.

SUMMARY OF THE INVENTION

In a first aspect, the present invention provides a device for promoting the healing of a topical stress crack in a predetermined skin portion of the body. The device includes a first means engageable with the skin portion of the body for drawing the stress crack together. A screen member attached to the first means and disposed intermediate with the skin crack and first means. Finally, a medical adhesive engageable with the screen member is used for sealing the stress crack.

In a further aspect, the present invention provides a method for promoting the healing of a topical stress crack. Such method comprises the steps of positioning the device and the screen member attached to an aperture in the device over the stress crack. The stress crack is closed by securing the device to the skin. A predetermined amount of medical adhesive is applied through the aperture. The medical adhesive is allowed to dry, and then the device is removed. The screen member and the medical adhesive remain attached to the closed stress crack for a predetermined amount of time, whereby the stress crack will be healed.

OBJECTS OF THE INVENTION

It is therefore a primary object of the present invention to provide a device for promoting the healing of topical stress cracks.

It is a further object of the present invention to provide a method for an individual to effectively treat a topical stress crack without assistance, since at least one hand is free to apply the application of the medical adhesive once the device is secured on the skin.

Still a further object of the present invention is to minimize the discomfort associated with an open stress crack during the healing process.

In addition to the various objects of the invention that have been described above, various other objects and advantages of the invention will become more readily apparent to those persons skilled in the relevant art from the following more detailed description of the invention, particularly, when such description is taken in conjunction with the attached drawing figures and the appended claims.

BRIEF DESCRIPTION OF THE DRAWINGS

FIG. 1 is a top view of a device for promoting the healing of a topical stress crack;

FIG. 2 is a partial sectional view taken along line II—II of FIG. 1; and

FIG. 3 is a bottom perspective view of a device for promoting the healing of a topical stress crack.

BRIEF DESCRIPTION OF A PRESENTLY PREFERRED AND VARIOUS ALTERNATIVE EMBODIMENTS OF THE PRESENT INVENTION

Prior to proceeding to a more detailed description of the invention, it should be noted that identical components having identical functions have been designated with identical reference numerals throughout the several views illustrated in the drawings for the sake of clarity.

Now refer more particularly to FIGS. 1, 2, and 3 of the drawings. Illustrated therein is a device, generally designated 10, for promoting the healing of a topical stress crack. The device 10 includes a first means 15 engageable with a skin portion of the body for drawing the stress crack together. The first means 15 is an adhesive element having a predetermined material, size, and shape. The first means 15 further includes an aperture 40 of a predetermined size and shape within the surface of the first means 15. The first means 15 includes at least one reinforcement member 35 to prevent material deformation of such first means 15. The reinforcement member 35 is disposed longitudinally along and engageable with such first means 15. Preferably, the device 10 includes two reinforcement members 35. An alternative embodiment includes one reinforcement member 35a disposed adjacent the circumference of the aperture 40 and engageable with such first means 15.

The device 10 further includes a screen member 20 is disposed intermediate with the skin crack and first means 15 for maintaining closure of the skin crack. The screen member 20 is a permeable, transparent, degradable material of a predetermined composition. The screen member 20 is attached to and overlaps the aperture 40 of such adhesive element 15.

Included further in the device 10 is a medical adhesive 25 engageable with the screen member 20 as a means for sealing such stress crack together. Preferably, the medical adhesive 25 is contained in an encapsulated unit 45 having a predetermined amount of such medical adhesive 25.

Further described herein is a method for promoting the healing of a stress crack. The method includes the positioning an adhesive element with a screen member and a liquid or fluid encapsulated unit of medical adhesive attached to an aperture over a stress crack. Securing the adhesive element to the skin closes the stress crack. The method further includes pressing the first end of the adhesive element to the skin, then pulling the second end of the adhesive element until the stress crack is closed. Pressing the second end of the adhesive element to the skin maintains closure of the stress crack.

A predetermined amount of medical adhesive is applied by releasing the encapsulated unit of medical adhesive through such aperture. Preferably, the medical adhesive is released through the aperture by applying pressure to the encapsulated unit. The medical adhesive is allowed to dry, then the adhesive element is removed. The screen member and the medical adhesive remain attached to the closed stress crack for a predetermined amount of time. An additional step includes trimming the screen member to fit such skin portion of the body. Preferably, the screen member is composed of a degradable material. After the predetermined amount of time has lapsed, the stress crack will be healed.

Although the invention has been shown in connection with a certain specific embodiment, it will be readily apparent to those skilled in the art that various changes in form and arrangement of parts and method may be made to suit requirements without departing from the spirit and scope of the invention.

I claim:

1. A device for promoting healing of a topical stress crack in a predetermined skin portion of a human body, said device comprising:
    a) a flexible adhesive element engageable with [such] said skin portion of said human body for drawing and maintaining said stress crack together for a predetermined amount of time;
    b) a screen member disposed intermediate with said stress crack and said flexible adhesive element for maintaining closure of said stress crack;
    c) at least one reinforcement member engageable with said flexible adhesive element for preventing material deformation of said flexible adhesive element; and
    d) a medical adhesive engageable with said screen member for sealing said stress crack together.

2. The device, according to claim 1, wherein said flexible adhesive element further includes an aperture having a predetermined size and shape disposed through said flexible adhesive element.

3. The device, according to claim 2, wherein said screen member is attached to and overlaps said aperture of said flexible adhesive element.

4. The device, according to claim 1, wherein said at lease one reinforcement member is disposed longitudinally along said flexible adhesive element.

5. The device, according to claim 4, wherein said device includes two reinforcement members.

6. The device, according to claim 1, wherein said at least one reinforcement member is disposed adjacent a circumference of said aperture and engageable with said flexible adhesive member.

7. The device, according to claim 6, wherein said at least one reinforcement member surrounds said aperture.

8. The device, according to claim 1, wherein said screen member is a permeable, transparent, degradable material having a predetermined composition.

9. The device, according to claim 1, wherein said medical adhesive is an encapsulated unit of a predetermined amount of medical adhesive.

10. A method for promoting healing of a stress crack, said method comprising the steps of:
    a) positioning a flexible adhesive element with a screen member and a fluid encapsulated unit of medical adhesive attached an aperture formed in said flexible adhesive element over said stress crack;
    b) closing said stress crack by securing said flexible adhesive element to skin adjacent said stress crack;
    c) applying a predetermined amount of medical adhesive by releasing a said encapsulated unit of medical adhesive through said aperture;
    d) allowing said medical adhesive to dry;
    e) removing said flexible adhesive element, wherein said screen member and said medical adhesive remain attached to a closed stress crack for a predetermined amount of time, whereby aid stress crack will be healed.

11. The method for prompting healing of a topical stress crack, according to claim 10, wherein step (b) of said method includes pressing a first end of said flexible adhesive element to said skin adjacent said stress crack, pulling a second end of said flexible adhesive element until said stress crack is closed, and pressing said second end of said flexible adhesive element to said skin to maintain closure of said stress crack.

12. The method for promoting healing of a topical top1cal stress crack, according to claim 10, wherein step (c) of said method includes applying pressure to said encapsulated unit to release said medical adhesive.

13. The method for promoting healing of a topical stress crack, according to claim 10, wherein step (e) of said method includes an additional step of trimming said screen member to fit said skin portion of said body.

14. The method for promoting healing of a topical stress crack, according to claim 10, wherein said method includes using a degradable material for said screen member.

* * * * *

UNITED STATES PATENT AND TRADEMARK OFFICE
CERTIFICATE OF CORRECTION

PATENT NO. : 6,410,818 B1
DATED : June 25, 2002
INVENTOR(S) : Michael F. Oyaski

It is certified that error appears in the above-identified patent and that said Letters Patent is hereby corrected as shown below:

Column 1,
Line 6, after "cracks", please delete the ","
Line 7, after, "and" first occurrence, please insert a comma -- , --
Line 27, after "intermediate", please delete "with"

Column 2,
Line 34, after "number 20", please delete "is"
Line 35, after "intermediate", please delete "with"

Column 3,
Line 13, after "with", please delete "[such]"

Column 4,
Line 11, after "attached", please insert -- to --
Line 16, after "releasing", please delete "a"
Line 21, after "whereby", please delete "aid" and insert -- said --
Line 31, after "topical", please delete "top1cal"

Signed and Sealed this

Twenty-fifth Day of November, 2003

JAMES E. ROGAN
*Director of the United States Patent and Trademark Office*